United States Patent [19]

Motoyama et al.

[11] Patent Number: 5,126,245

[45] Date of Patent: Jun. 30, 1992

[54] REAGENTS FOR ASSAY OF GAMMA-GLUTAMYLTRANSPEPTIDASE

[75] Inventors: Akio Motoyama; Hitoshi Kondo; Takanari Shiraishi; Kazuhiko Nagata; Kosuke Tomita, all of Kyoto, Japan

[73] Assignee: Unitika Ltd., Hyogo, Japan

[21] Appl. No.: 105,773

[22] Filed: Oct. 7, 1987

[30] Foreign Application Priority Data

Oct. 7, 1986 [JP] Japan ................. 61-239648

[51] Int. Cl.$^5$ .................. C12Q 1/48; C12Q 1/52; C12P 21/02
[52] U.S. Cl. ...................... 435/15; 435/16; 435/24; 435/26; 435/71.1
[58] Field of Search ............ 435/15, 16, 24, 26, 435/70, 803, 810

[56] References Cited

U.S. PATENT DOCUMENTS 4,024,021 5/1977 Stavropoulos et al. ...... 195/103.5 R
4,511,651 4/1985 Beaty et al. ................ 435/15

FOREIGN PATENT DOCUMENTS 0152274 6/1985 European Pat. Off. .
0218140 9/1986 European Pat. Off. .

OTHER PUBLICATIONS

International Union of Biochemistry, 1978, Enzyme Nomenclature, pp. 158–159, No. 2.3.2.2. Academic Press, New York.
Lehninger, Biochemistry, 2nd Edition, 1975 p. 795.
AMERICAN JOURNAL OF CLINICAL PATHOLOGY, vol. 34, No, 4, Oct. 1960, pp. 381-398, US; R. J. Henry et al. "Revised spectrophotomertic methods for the determination of gluamic-oxalacetic transaminase, glutamic-pyruvic transaminase, and lactic acid dehydrogenase".

*Primary Examiner*—Christine Nucker
*Assistant Examiner*—Laurie A. Scheiner
*Attorney, Agent, or Firm*—Sughrue, Mion, Zinn, Macpeak & Seas

[57] ABSTRACT

A reagent for assaying γ-glutamyltranspeptidase (γ-GTP) which contains an amino acid dehydrogenase and a substrate specific to γ-glutamyltranspeptidase activity. The reagent can be used to assay the γ-GTP activity directly from the continuous course of reaction without using a standard substance with known activity. The procedure required is simple and easy, and the reagent is capable of determining γ-GTP activity with good accuracy and without being affected by interfering substances, making it satisfactory for routine use in clinical laboratories.

14 Claims, 2 Drawing Sheets

REAGENTS FOR ASSAY OF GAMMA-GLUTAMYLTRANSPEPTIDASE

FIELD OF THE INVENTION

This invention relates to reagents for the assay of γ-glutamyltranspeptidase activity in body fluids.

BACKGROUND OF THE INVENTION

γ-Glutamyltranspeptidase (hereinafter abbreviated as γ-GTP) is an enzyme widely distributed in tissues of organisms and involved in the metabolism of γ-glutamylpeptides. In the area of clinical laboratory testing, the γ-GTP activity is an important test that is widely and routinely employed in the diagnosis of hepatic diseases such as hepatocirrhosis, alcoholic hepatitis, hepatoma and obstructive jaundice and in disease state monitoring in patients suffering from such diseases.

In reagents generally used for the determination of γ-GTP activity, a γ-glutamylamide, which is a synthetic substrate, is used as the γ-glutamyl donor and the amine liberated by the action of γ-GTP is determined. As typical examples, reagents in which γ-glutamyl-p-nitroanilide is used as the substrate (cf. Japanese Patent Application (OPI) No. 99198/80 (the term "OPI" as used herein means an "unexamined published Japanese patent application")), and reagent systems in which γ-glutamyl-α-naphthylamide is used as the substrate (cf. Japanese Patent Application (OPI) No. 6392/75) are known. With the former substrate, either the p-nitroaniline liberated by the action of γ-GTP is directly assayed by colorimetry or the p-nitroaniline is converted into a red-colored substance using an aldehyde such as p-dimethylaminocinnamaldehyde, which is then assayed by colorimetry. In the reagents using γ-glutamyl α-naphthylamide as the substrate, the naphthylamine liberated by the action of γ-GTP is converted to a diazonium salt, which is then assayed by colorimetry, or is oxidatively coupled with 3-methyl-2-benzothiazolinone hydrazone to give a reddish-purple substance, which is then assayed colorimetrically.

Reagents for γ-GTP activity assay which use a conjugate enzyme have also been proposed. In one of them, a γ-glutamyl-organic group-substituted methylamide compound is used as the substrate, and the substituted methylamine compound formed by the action of γ-GTP is brought into contact with amine oxidase, and the consumption of dissolved oxygen or yield of hydrogen peroxide or ammonia resulting from the progress of the enzymatic reaction is quantitatively determined by a conventional method (cf. British Patent 2,103,607). In Japanese Patent Application (OPI) No. 34200/85, it is proposed that γ-glutamyl-L-glutamic acid, which is close in nature to naturally occurring substances, be used as the substrate, that the L-glutamate liberated by the action of γ-GTP be brought into contact with L-glutamate oxidase, and that the consumption of dissolved oxygen or yield of hydrogen peroxide, ammonia or α-ketoglutarate be determined by a conventional method.

However, each of the reagents for γ-GTP assay using the above-mentioned synthetic substrates has its drawbacks. For instance, γ-glutamyl-p-nitroanilide and similar substances have very poor solubility in the pH range in which these compounds are stable and in the neighborhood of the optimum pH for γ-GTP reaction, making it difficult to use the substrates in sufficient amounts. Furthermore, these synthetic substrates are not very stable. In addition, they cause absorbance changes in the wavelength region in which bilirubin and/or hemolysis (hemoglobin) is significant and this makes it difficult to obtain exact assay results. The assay reagents using γ-glutamyl-α-naphthylamide as a substrate have the further disadvantage that the procedure is complicated.

A number of measures for overcoming these drawbacks have been proposed (e.g., use of surfactants (cf. Japanese Patent Application (OPI) No. 103352/83), use of variously substituted substrates (cf. British Patent 2,103,607 and European Patent 152,274/85), addition of cyclodextrin (cf. U.S. Pat. No. 4,511,651). However, the problems have not yet been solved to an extent such that the measures can be widely practiced in routine clinical testing.

The enzymatic assay reagents which use amine oxidase or L-glutamate oxidase are also disadvantageous since these enzymes have relatively low substrate specificity, and the absorbance in the measuring wavelength region is strongly influenced by bilirubin and/or hemoglobin coexisting in blood or urine. They therefore lack reliability from the viewpoint of routine use in clinical laboratories.

Furthermore, each of the above-described conventional assay systems requires a complicated or troublesome procedure because of the necessity of using a standard substance with known activity.

Thus, it would be highly desirable to develop a reagent for the assay of γ-GTP which uses, as the substrate, a peptide compound analogous to natural substrates for γ-GTP permitting the γ-GTP activity to be determined directly from the continuous course of reaction by a simple and easy procedure.

SUMMARY OF THE INVENTION

Accordingly, it is an object of the invention to provide a reagent for the assay of γ-GTP with which the γ-GTP activity can be determined directly from the continuous course of reaction by a simple procedure.

As a result of intensive investigations in an attempt to provide a reagent for γ-GTP assay which can meet such requirements, the present inventors have found that an assay reagent in which a substrate specific to γ-GTP activity is used as the substrate and an amino acid dehydrogenase is used as a conjugate enzyme can achieve the above object, can be used with ease and simplicity and can give results that are sufficiently accurate from the routine test standpoint. Based on these findings, the inventors have now completed the present invention.

Thus the invention lies in a reagent for γ-GTP assay which/contains an amino acid dehydrogenase and a substrate specific to γ-GTP activity.

DETAILED DESCRIPTION OF THE INVENTION

Figure 1:
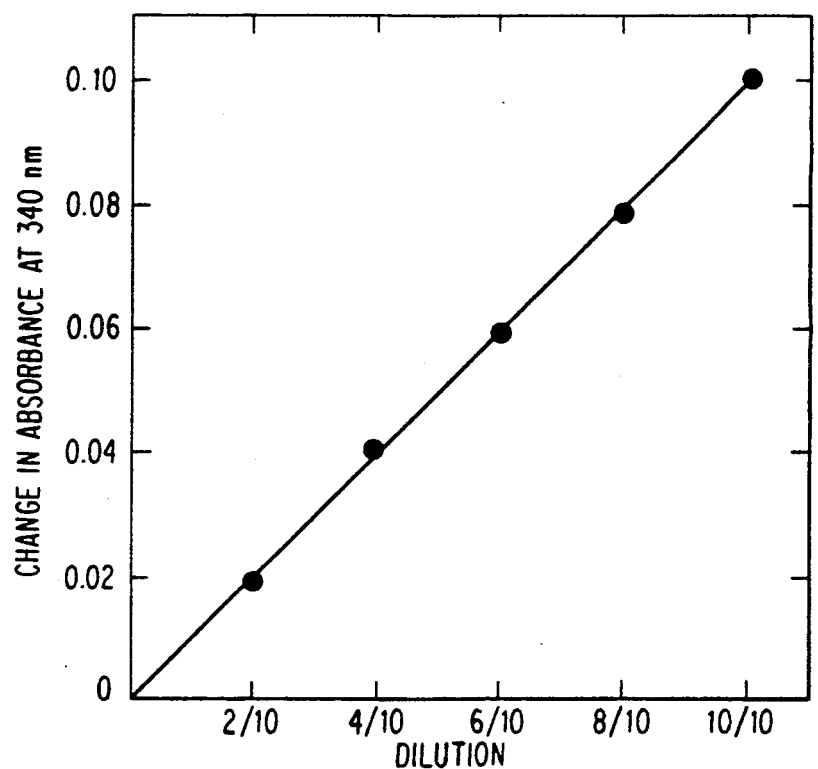
FIGS. 1 to 4 illustrate the reagent according to the invention, by plotting change in absorbance at 340 nm per minute against the degree of dilution of samples.

The reagents according to the invention are a novel reagent for λ-GTP assay in which an amino acid dehydrogenase and a substrate specific for γ-GTY are used. It overcomes the substrate-associated problems so far encountered with the conventional synthetic substrates.

Unlike conventional reagents, it is not influenced by coexisting substances in blood, such as bilirubin and hemoglobin. It does not require any complicated or troublesome procedure, and hence renders the assay procedure improved in operability or workability. Furthermore, the use of the reagents according to the invention result in sufficient reproducibility for making it useful for routine test purposes.

Thus the reagents according to the invention are a great contribution to the field of clinical laboratory testing.

In accordance with the invention, the reagents for assaying γ-GTP contain an amino acid dehydrogenase, a substrate specific to γ-GTP, an acceptor and nicotinamide adenine dinucleotide (phosphate) (hereinafter abbreviated as NAD(P)+), which are principal essential components. It may further include conventional optional additives in ordinary use, such as a promoter and an activator. Thus, for instance, promoters such as hydrazine, semicarbazide, etc., which can promote amino acid dehydrogenase reaction, salts such as sodium chloride, potassium chloride, magnesium chloride, etc., or polyoxyethylene-type non-ionic surfactants (e.g., Triton X-100, etc.) which can contribute to the stability and storability of the substrate such as γ-glutamyldipeptide and NAD(P)+, etc., and preservatives such as known sodium azide, sorbic acid, etc., can be used without any trouble. Also, as the stabilizer of enzymes, sugars such as mannitol, etc., albumin, polyols such as glycerin, etc., can be suitably used.

The amino acid dehydrogenase used in the invention includes leucine dehydrogenase, alanine dehydrogenase, glutamate dehydrogenase, phenylalanine dehydrogenase, glycine dehydrogenase, valine dehydrogenase and serine dehydrogenase. Among them, the first-mentioned three are preferred. The substrate specific to γ-GTP is preferably a γ-glutamyldipeptide and the like, for example, γ-glutamyl-L-leucine, γ-glutamyl-L-alanine, γ-glutamyl-L-glutamic acid, γ-glutamyl-L-phenylalanine, glutamyl-L-glycine, γ-glutamyl-L-valine and γ-glutamyl-L-serine, corresponding to the above-described amino acid dehydrogenases. Further, as the substance (called acceptor) which acts to receive the γ-glutamyl group from various γ-glutamyldipeptides as the substrate by the action of γ-GTP, various amino acids and dipeptides can be used. Among them, it is preferable to use as the acceptor methionine, glycylglycine, or glycylalanine which have high acceptability for the γ-glutamyl group.

The leucine dehydrogenase used in the invention may be of any origin. Thus leucine dehydrogenase species of various origins, for example, microorganisms of the genus Bacillus such as *Bacillus sphaericus* (e.g., IFO 3325, IFO 3526, etc.), *Bacillus cereus* (e.g., IFO 3001), *Bacillus subtilis* (e.g., IFO .3037, etc.), *Bacillus brevis* (e.g., IFO 3331, etc.), etc.; and microorganisms such as *Staphylococcus aureus* (e.g., IFO 3060, etc.) can be used. Leucine dehydrogenases species derived from thermophilic bacteria which have good stability and storability, such as *Bacillus stearothermophilus* (e.g., IFO 12550, IFO 12983, etc.), *Clostridium thermoaceticum*, etc., are desirable among others. These leucine dehydrogenases can be prepared by an appropriate combination of the known techniques of extraction, purification, etc., especially by, for example, the process as disclosed in Archives of *Microbiology*, vol. 141, pages 407–411 (1985).

The alanine dehydrogenase, too, may be of any origin, and various species derived, for example, from microorganisms such as *Bacillus subtilis* (e.g., IFO 3009, etc.), *Bacillus sphaericus* (e.g., IFO 3325, IFO 3526, etc.), *Streptomyces phaeothromogenes* (e.g., IFO 3149, etc.), etc., can be used. Desirable among others are the alanine dehydrogenase species derived from the thermophilic bacteria which have good stability and storability, such as *Bacillus stearothermophilus* (e.g., IFO 12550, etc.). These alanine dehydrogenases can be prepared by an appropriate combination of the known techniques of extraction, purification, etc., especially by, for example, the process as disclosed in European Journal of *Biochemistry*, vol. 100, pages 29–39 (1979).

Furthermore, the glutamate dehydrogenase may be of any origin, and species derived from various origins, for example, microorganisms, inclusive of bacteria such as *Proteus inconstans* (e.g., IFO 12930, etc.), *Peptococcus aurogenes* (e.g., ATCC 14963, etc.), etc., fungi such as *Dictyostelium discoideum*, etc., and yeasts such as *Neurospora crassa, Saccharomyces cerevisiae, Candida utilis*, etc., as well as plants such as peas, soybeans, etc. and animal organs such as ox liver, etc., can be used. These enzymes can be prepared by an appropriate combination of the known techniques of extraction, purification, etc., especially by, for example, the process as disclosed in *Journal of Fermentation Technology*, vol. 57, pages 428–433 (1979).

The amount of these amino acid dehydrogenases can be expressed in terms of activity units of these enzymes. One unit of activity of an enzyme is defined as the amount of the enzyme that forms 1 μmol of the product per minute at 30° C. The activity of these enzymes can be determined according to known methods, and, for example, according to the method described in *Journal of Biological Chemistry*, vol. 253, pages 5719–5725 (1978), the leucine dehydrogenase, according to the method described in *Methods of Enzymatic Analysis* (ed. by H. U. Bergmeyer), Verlag. Chemie International (U.S.A.), pages 427–428 (1974), the alanine dehydrogenase, and according to the method described in *Journal of Fermentation Technology*, vol. 57, pages 428–433 (1979), the glutamic acid dehydrogenase can be determined The individual components included in the reagents according to the invention are used in the following concentrations: 3 to 300 mM γ-glutamyldipeptide (e.g., in the case of γ-glutamyl-L-leucine 3 to 150 mM; in the case of γ-glutamyl-L-alanine 10 to 300 mM; in the case of γ-glutamyl-L-glutamic acid 3 to 300 mM), more preferably 7.5 to 250 mM γ-glutamyldipeptide (e.g.; in the case of γ-glutamyl-L-leucine 7.5 to 100 mM; in the case of γ-glutamyl-L-alanine 15 to 250 mM; in the case of γ-glytamyl-L-glutamic acid 7.5 to 250 mM); 3 to 500 mM acceptor, more preferably 5 to 350 mM acceptor; 0.1 to 20 mM NAD(P)+, more preferably 0.2 to 15 mM NAD(P)+; 5 to 500 mM salts, more preferably 10 to 350 mM salts; 0.01 to 2 wt. % surfactant, more preferably 0.02 to 1.5 wt. % surfactant; 0.5 to 50 mM sodium azide, more preferably 1.0 to 30 mM sodium azide; and 0.1 to 100 units of amino acid dehydrogenase per milliliter, more preferably 0.2 to 50 units of amino acid dehydrogenase per milliliter.

In the case where these reagent components are used immediately after their preparation, the preservatives such as sodium azide need not be added.

The reagent in the present invention can be used as the so-called one reagent system containing all of the above-described reagent components, but in other cases it can also be used in such a way that the above-described reagent components are first divided into two reagents and then the two reagents are mixed when in use (two-reagent system). One specific example of the latter case is a reagent system comprising the first reagent containing amino acid dehydrogenase, acceptor, salts, surfactant, and preservative, and the second reagent containing γ-glutamyldipeptide, NAD(P)+, salts, surfactant, and preservative. This invention, of course, is not limited to the above specific example, and various reagent system forms can be employed.

The principle on which the reagent system according to the invention works may be illustrated as follows:

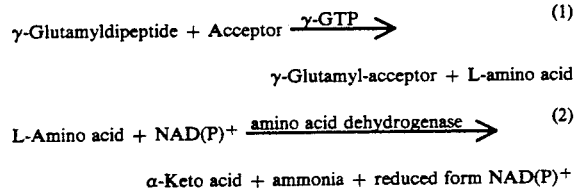

Thus the γ-GTP activity can be determined by continuously measuring the increase in absorbance due to the reduced form of NAD(P)+ (hereinafter abbreviated as NAD(P)H at 340 nm. This is a stoichiometric method which is carried out in the art when a reaction system is accompanied by changes in absorption of NAD(P)H, wherein the molecular extinction coefficient is measured at 340 nm that is specifically defined, thereafter the amount of NAD(P)H formed is found from the changes in absorption of NAD(P)H by the aid of the molecular extinction coefficient and this is regarded as the amount of the product formed by the enzymatic reaction.

Furthermore, it is possible to employ a method comprising converting the NAD(P)H formed in accordance with equation (2) into diformazan by a reaction with one member selected from among diaphorase, phenazine methosulfate and 1-methoxyphenazine methosulfate.

In determining the γ-GTP activity in body fluids such as serum and urine using the reagent system according to the invention, a reaction temperature of 20° to 45° C. is used, as is usual for ordinary enzymatic reactions.

The typical examples of the body fluids that can be analyzed using the reagent according to the present invention include serum, urine, spinal fluid, pancreatic juice, bile, ascites, extracts from the liver and the kidney, feces, etc.

The following examples illustrate the invention in further detail, but the present invention is not to be construed as being limited thereto. Unless otherwise indicated, all parts, percents and ratios are by weight.

EXAMPLE 1

A reagent for the assay of γ-GTP was prepared which comprised 20 mM γ-glutamyl-L leucine (purchased from Bachem A.G.), 75 mM glycylglycine (pH 8.5), 6 mM NAD (purchased from Boehringer Mannheim Yamanouchi Co., Ltd.) and 5 units/milliliter of leucine dehydrogenase (derived from Bacillus sp.; purchased from Toyobo Co., Ltd.).

A 3.0-milliliter portion of the above reagent was placed in a cell (optical path length 1 cm), 0.05 milliliter of a control Serum was added, and the γ-GTP activity of the sample was determined through the change in absorbance at 340 nm using a spectrophotometer with its cell chamber maintained at a constant temperature of 37° C. In addition, as the sample a control serum having γ-GTP activity (High Level Chek-E) was purchased (from International Reagent Corporation), and made into a solution of about 1,000 units/liter before use. The serum containing γ-GTP in an optional concentration was prepared by diluting the above-obtained solution of control serum with 0.9% saline solution. The results obtained are shown in FIG. 1.

The data are shown in FIG. 1, which illustrates the quantitative feature of the reagent according to the invention. The change in absorbance at 340 nm per minute on the ordinate and the degree of dilution of the serum sample on the abscissa indicate that the reagent gives good linearity.

EXAMPLE 2

The same reagent for γ-GTP assay as that of Example 1 was prepared.

A control system sample containing 40 or 100 units/liter of γ-GTF was assayed for γ-GTP activity using the reagent. Fifty assay runs were repeated with each sample.

The mean assay values were 39.7 and 101.1 units/liter, with standard deviations of 1.0 and 1.3 units/liter, respectively.

Thus the C.V. values ((standard deviation/mean assay value)×100 (%)), which are indicative of the accuracy of the assay, were 2.52% and 1.29%, respectively, indicating that the reagent according to the invention provides sufficiently accurate results.

EXAMPLE 3

The same reagent for γ-GTP assay as that of Example 1 was prepared.

Serum samples having a γ-GTP activity of 40 units/liter and containing 0 to 20 mg/deciliter of ascorbic acid (purchased from Ishizu Seiyaku Co., Ltd.), 0 to 20 mg/deciliter of uric acid (purchased from Ishizu Seiyaku Co., Ltd.), 0 to 20 mg/deciliter of glutathione (purchased from Ishizu Seiyaku Co., Ltd.), 0 to 1,000 mg/deciliter of glucose (purchased from Nakarai Chemicals, Ltd.), 0 to 20 mg/deciliter of bilirubin (purchased from International Reagent Corporation) and 0 to 500 mg/deciliter of hemoglobin (hemoglobin control Hemocon N; purchased from Nippon Shoji Kaisha Ltd.) were prepared.

These samples were assayed for γ-GTP activity with the above reagent.

As a result, it was found that the γ-GTP activity assay results obtained using the invention reagent were not influenced by any of ascorbic acid (up to 20 mg/deciliter), uric acid (up to 20 mg/deciliter), glutathione (up to 20 mg/deciliter), glucose (up to 1,000 mg/deciliter), bilirubin (up to 20 mg/deciliter) and hemoglobin (up to 500 mg/deciliter). Accordingly, the present invention reagent avoids positive errors due to these substances found with conventional reagents which use a synthetic substrate and/or an enzymatic reaction. The unexpected superiority of the reagent according to the invention is confirmed by these results.

EXAMPLE 4

A γ-GTP assay reagent system was prepared in the same manner as in Example 1 except that glycylalanine (pH 8.5, 100 mM) was used instead of glycylglycine.

The reagent was used for γ-GTP activity determination in the same manner as in Example 1.

Figure 2:
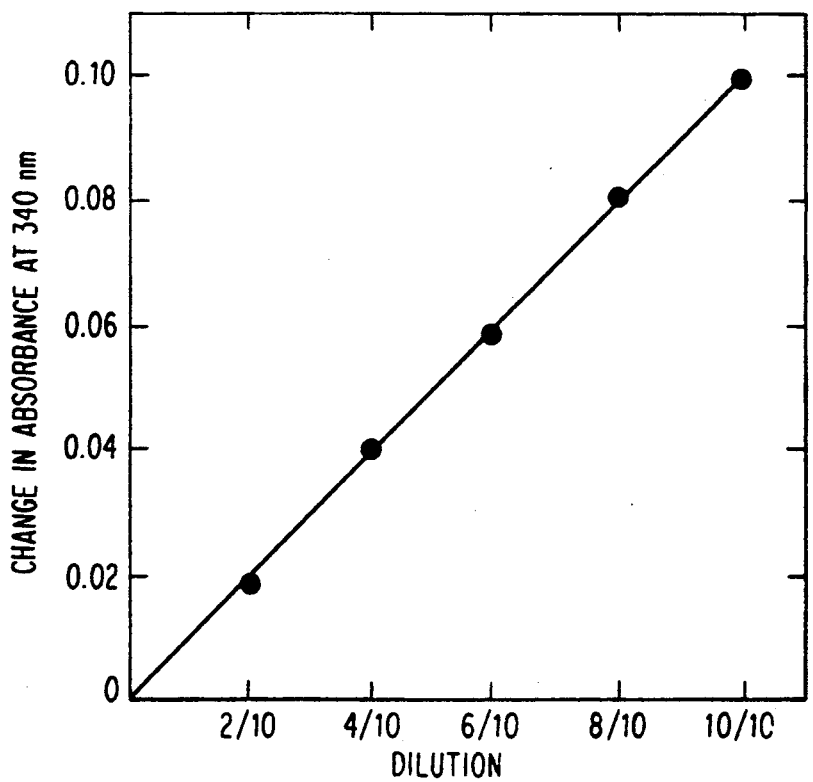

The results obtained are shown in FIG. 2.

FIG. 2, which illustrates the quantitative features of the reagent according to the invention, demonstrates that the reagent has an assay range sufficient for practical use and satisfactory performance.

EXAMPLE 5

A γ-GTP assay reagent was prepared which comprised 50 mM γ-glutamyl-L-alanine (purchased from Bachem A.G.), 100 mM (pH 8.5) glycylglycine, 5 mM NAD and 6 units/milliliter of alanine dehydrogenase (derived from *Bacillus subtilis;* purchased from Sigma Chemical Company).

This was used for γ-GTP activity determination in the same manner as in Example 1.

Figure 3:
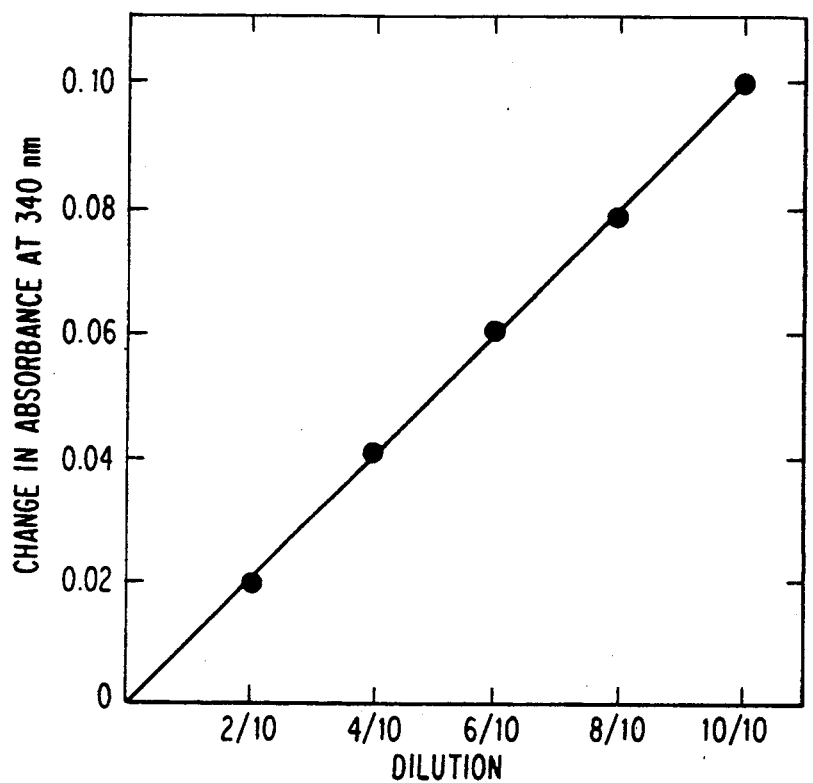

The results obtained are shown in FIG. 3.

FIG. 3, which illustrates the quantitative features of the reagent according to the invention, demonstrates that the reagent has an assay range sufficient for practical use and satisfactory performance.

EXAMPLE 6

A γ-GTP reagent was prepared which comprised 20 mM γ-glutamyl-L-glutamic acid (purchased from Bachem A.G.), 75 mM glycylglycine (pH 8.5), 1.5 mM NAD(P)+ (purchased from Boehringer Mannheim Yamanouchi Co., Ltd.) and 5 units/milliliter of glutamate dehydrogenase (derived from Proteus sp.; purchased from Toyobo Co., Ltd.).

This was used for γ-GTP activity determination in the same manner as in Example 1.

Figure 4:
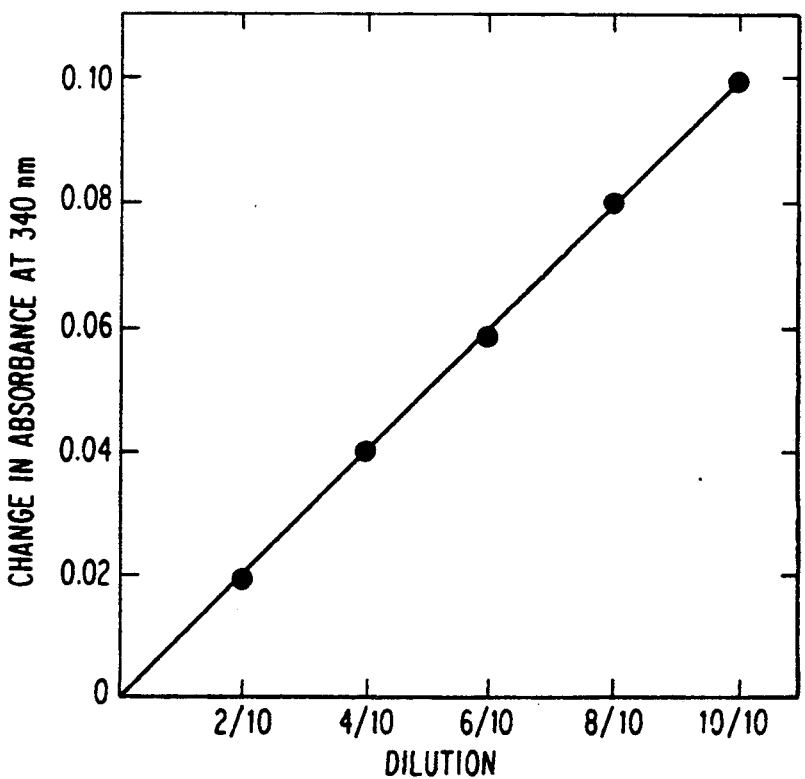

The results obtained are shown in FIG. 4.

FIG. 4, which illustrates the quantitative features of the reagent according to the invention, demonstrates that the reagent is satisfactory in performance, so that it can be put to practical use.

While the invention has been described in detail and with reference to specific embodiments thereof, it will be apparent to one skilled in the art that various changes and modifications can be made therein without departing from the spirit and scope thereof.

What is claimed is:

1. A reagent for assaying γ-glutamyltranspeptidase comprising an amino acid dehydrogenase selected from the group consisting of leucine dehydrogenase, valine dehydrogenase and alanine dehydrogenase and a γ-glutamyl-dipeptide.

2. The reagent according to claim 1, wherein said γ-glutamyldipeptide is selected from the group consisting of γ-glutamyl-L-leucine, γ-glutamyl-L-alanine, and γ-glutamyl-L-valine.

3. The reagent according to claim 1, wherein said amino acid dehydrogenase is leucine dehydrogenase.

4. The reagent according to claim 1, wherein said amino acid dehydrogenase is alanine dehydrogenase.

5. A reagent for assaying γ-glutamyltranspeptidase comprising an amino acid dehydrogenase selected from the group consisting of leucine dehydrogenase, valine dehydrogenase and alanine dehydrogenase, a γ-glutamyldipeptide, an acceptor for a γ-glutamyl group, and nicotinamide adenine dinucleotide phosphate.

6. The reagent according to claim 5, wherein said acceptor is an amino acid or a dipeptide.

7. The reagent according to claim 6, wherein said amino acid is methionine.

8. The reagent according to claim 5, wherein said reagent comprises 0.1 to 100 units of said amino acid dehydrogenase, 3 to 300 mM of said γ-glutamyldipeptide, 3 to 500 mM of said acceptor and 0.1 to 20 mM of said nicotinamide adenine dinucleotide phosphate per milliliter of said reagent.

9. The reagent according to claim 8, wherein said reagent comprises 0.2 to 50 units of said amino acid dehydrogenase, 7.5 to 250 mM of said γ-glutamyldipeptide, 5 to 300 mM of said acceptor, and 0.2 to 15 mM of said nicotinamide adenine dinucleotide phosphate per milliliter of said reagent.

10. The reagent according to claim 8, further comprising from 5 to 500 mM of a salt, from 0.01 to 2 wt. % of a surfactant, and from 0.5 to 50 mM of sodium azide per milliliter of said reagent.

11. The reagent according to claim 9, further comprising, from 10 to 350 mM of a salt, from 0.02 to 1.5 wt. % of a surfactant, and from 1.0 to 30 mM of sodium azide per milliliter of said reagent.

12. A method for determining γ-glutamyltranspeptidase activity comprising the steps of:
  (a) reacting a γ-glutamyldipeptide selected from the group consisting of γ-glutamyl-L-leucine, γ-glutamyl-L-valine and γ-glutamyl-L-alanine and an acceptor for a γ-glutamyl group in the presence of a sample containing γ-glutamyltranspeptidase to produce a γ-glutamyl-acceptor and an L-amino acid;
  (b) reacting said L-amino acid and nicotinamide adenine dinucleotide phosphate in the presence of an amino acid dehydrogenase selected from the group consisting of leucine dehydrogenase, valine dehydrogenase and alanine dehydrogenase to produce an α-keto acid, ammonia and the reduced form of nicotinamide adenine dinucleotide; and
  (c) determining the γ-glutamyltranspeptidase activity corresponding to the concentration of said reduced form of nicotinamide adenine dinucleotide phosphate.

13. The method as claimed in claim 12, wherein said γ-glutamyltranspeptidase activity is determined by measuring the increase in absorbance of the reduced form of nicotinamide adenine dinucleotide phosphate at a wavelength of 340 nm.

14. The reagent according to claim 6, wherein said dipeptide is selected from the group consisting of glycylglycine and glycylalanine.

* * * * *